US011241288B2

(12) United States Patent
Xu et al.

(10) Patent No.: US 11,241,288 B2
(45) Date of Patent: Feb. 8, 2022

(54) FLEXIBLE SURGICAL INSTRUMENT SYSTEM

(71) Applicant: BEIJING SURGERII TECHNOLOGY CO., LTD., Beijing (CN)

(72) Inventors: Kai Xu, Beijing (CN); Zhengchen Dai, Beijing (CN); Huichao Zhang, Beijing (CN); Shu'an Zhang, Beijing (CN); Jiangran Zhao, Beijing (CN); Zhixiong Yang, Beijing (CN); Wei Wei, Beijing (CN)

(73) Assignee: BEIJING SURGERII TECHNOLOGY CO., LTD, Beijing (CN)

( * ) Notice: Subject to any disclaimer, the term of this patent is extended or adjusted under 35 U.S.C. 154(b) by 338 days.

(21) Appl. No.: 16/329,733

(22) PCT Filed: Aug. 30, 2017

(86) PCT No.: PCT/CN2017/099756
§ 371 (c)(1),
(2) Date: Feb. 28, 2019

(87) PCT Pub. No.: WO2018/041160
PCT Pub. Date: Mar. 8, 2018

(65) Prior Publication Data
US 2019/0192242 A1  Jun. 27, 2019

(30) Foreign Application Priority Data
Aug. 31, 2016 (CN) .......................... 201610796098.5

(51) Int. Cl.
*A61B 34/30* (2016.01)
*A61B 17/00* (2006.01)
(Continued)

(52) U.S. Cl.
CPC ............ *A61B 34/30* (2016.02); *A61B 1/0016* (2013.01); *A61B 17/00* (2013.01); *A61B 34/71* (2016.02);
(Continued)

(58) Field of Classification Search
CPC .............. A61B 34/71; A61B 2034/715; A61B 2034/306; A61B 2034/301;
(Continued)

(56) References Cited

U.S. PATENT DOCUMENTS 5,710,870 A * 1/1998 Ohm .......................... B25J 3/04
700/245
2007/0043338 A1* 2/2007 Moll ..................... A61B 17/062
606/1
(Continued)

FOREIGN PATENT DOCUMENTS

CN 103085083 A 5/2013
CN 103315781 A 9/2013
(Continued)

OTHER PUBLICATIONS

ISA State Intellectual Property Office of the People's Republic of China, International Search Report Issued in Application No. PCT/CN2017/099756, dated Nov. 27, 2017, WIPO, 4 pages.
(Continued)

*Primary Examiner* — Katherine H Schwiker
(74) *Attorney, Agent, or Firm* — McCoy Russell LLP

(57) ABSTRACT

Disclosed is a flexible surgical instrument system, comprising a distal structural body comprising at least one distal structural segment each comprising a distal spacing disk, a fixing disk and structural backbones; a proximal structural body comprises at least one proximal structural segment each comprising a proximal spacing disk, a proximal fixing disk and structural backbones; a plurality of cable transmission mechanisms each comprising a gear set and a pulley-cable part, the gear set being operable to transfer a rotational motion to the pulley-cable part; and a driving unit comprising a motion transmission part comprising a plurality of proximal segment turning transmission chains to convert a rotational output into mutually reversed rotational motions,
(Continued)

and transfer one of the mutually reversed rotational motions to one of the gear sets.

18 Claims, 11 Drawing Sheets

(51) Int. Cl.
*A61B 34/00* (2016.01)
*A61B 1/00* (2006.01)

(52) U.S. Cl.
CPC ..... *A61B 1/00133* (2013.01); *A61B 2034/301* (2016.02)

(58) Field of Classification Search
CPC ........... A61B 2017/00323; A61B 2017/00327; A61B 2017/00318; A61B 2017/00305–00314; A61B 2017/003
See application file for complete search history.

(56) References Cited

U.S. PATENT DOCUMENTS

| | | | |
|---|---|---|---|
| 2009/0247944 A1* | 10/2009 | Kirschenman | A61B 90/10 604/95.04 |
| 2012/0172703 A1* | 7/2012 | Esguerra | A61B 5/062 600/409 |
| 2013/0090763 A1* | 4/2013 | Simaan | A61B 5/11 700/258 |
| 2014/0330432 A1* | 11/2014 | Simaan | A61B 34/35 700/250 |
| 2014/0350337 A1 | 11/2014 | Simaan et al. | |
| 2015/0216546 A1 | 8/2015 | Krause et al. | |
| 2015/0352728 A1 | 12/2015 | Wang | |
| 2016/0135914 A1* | 5/2016 | Isoda | A61B 34/72 606/130 |

FOREIGN PATENT DOCUMENTS

| | | | |
|---|---|---|---|
| CN | 103519772 A | | 1/2014 |
| CN | 103948435 A | * | 7/2014 |
| CN | 103948435 A | | 7/2014 |
| CN | 105751210 A | * | 7/2016 |
| CN | 105751210 A | | 7/2016 |
| CN | 106361432 A | | 2/2017 |
| WO | 2009094670 A1 | | 7/2009 |

OTHER PUBLICATIONS

State Intellectual Property Office of the People's Republic of China, Office Action and Search Report Issued in Application No. 201610796098.5, dated May 22, 2018, 8 pages.
European Patent Office, Supplementary European Search Report Issued in Application No. 17845462.5, dated Apr. 2, 2020, Germany, 2 pages.

* cited by examiner

FLEXIBLE SURGICAL INSTRUMENT SYSTEM

CROSS REFERENCE TO RELATED APPLICATIONS

The present patent application is a U.S. National Phase of Chinese International Application No. PCT/CN2017/099756 entitled "FLEXIBLE SURGICAL INSTRUMENT SYSTEM", and filed on Aug. 30, 2017. Chinese International Application No. PCT/CN2017/099756 claims priority to Chinese Patent Application No. 201610796098.5 filed on Aug. 31, 2016. The entire contents of each of the above-identified applications are incorporated herein by reference for all purposes.

TECHNICAL FIELD

The present invention relates to a flexible surgical instrument system capable of passing through a single surgical incision, belonging to the field of medical instruments.

BACKGROUND ART

Multi-port laparoscopic minimally invasive surgery has occupied an important position in surgery because of it having small wound and rapid postoperative recovery. The existing da Vinci surgical robot of the Intuitive Surgical, Inc. assists doctors in implementing the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been further developed and have less trauma to the patient and higher postoperative outcomes. However, in the single-port laparoscopic surgery and the natural orifice transluminal non-invasive surgery, all surgical instruments including a visual illumination module and a surgical manipulator have access to the surgical site through a single channel, which is extremely stringent for the preparation of the surgical instruments. A distal structure of the existing surgical instrument is mainly of multiple rods articulated in series, and is driven by a pulling force from a steel wire rope, so that the surgical instrument can turn at an articulated joint. Since the steel wire rope has to be continuously tensioned by a pulley, this driving method can hardly lead to further miniaturization of the surgical instrument, and also further improvement of the moving performance of the instrument.

Although the Intuitive Surgical, Inc. recently introduced a da Vinci Single-Site (SS-type da Vinci) surgical robot, in which the original rigid surgical instrument is modified into a semi-rigid surgical instrument and a pre-bent sleeve is additionally provided so as to improve the moving performance of the surgical instrument to a certain extent, it is impossible to fundamentally solve the problems faced by the traditional surgical instruments.

SUMMARY OF THE INVENTION

In view of the above problems, an object of the present invention is to provide a flexible surgical instrument system capable of passing through a single surgical incision that can be better applied to a surgical robot system that passes through a natural orifice of the human body or a single surgical incision and performs surgery.

In order to achieve the above-mentioned object, the following technical solutions are used in the present invention: a flexible surgical instrument system, comprising a flexible surgical instrument, wherein the flexible surgical instrument comprises a flexible continuous body structure composed of a distal structural body, a proximal structural body and a middle connecting body; the distal structural body comprises at least one distal structural segment comprising a distal spacing disk, a distal fixing disk and structural backbones; the proximal structural body comprises a proximal structural segment comprising a proximal spacing disk, a proximal fixing disk and structural backbones; the middle connecting body comprises channel fixing plates and a structural backbone guide channel provided between the channel fixing plates; the structural backbones of the distal structural segment are securely connected, in one-to-one correspondence, to or are the same as the structural backbones of the proximal structural segment, one end of each of the structural backbones is securely connected to the proximal fixing disk, passing through the proximal spacing disk, the structural backbone guide channel, and the distal spacing disk in sequence, and the other end of the structural backbones is securely connected to the distal fixing disk; and a driving unit fixing plate is arranged behind the channel fixing plates, a plurality of cable transmission mechanisms for converting a rotational motion input into a linear motion output are arranged between the driving unit fixing plate and the channel fixing plate, an output end of each of the cable transmission mechanisms is connected to one end of a driving backbone via a linear motion mechanism, and the other end of the driving backbone passes through the proximal spacing disk and is then securely connected to the proximal fixing disk.

Preferably, the number of the proximal structural segments is equal to the number of the distal structural segments.

In one embodiment, the cable transmission mechanism may comprise a male coupling, a first bevel gear, a second bevel gear, a fixing block, a first pulley, a second pulley, a pulley seat, a guiding rod, a driving cable and a guiding slider, wherein the male coupling is rotatably arranged on the driving unit fixing plate and has a front end thereof coaxially and securely connected to the first bevel gear, the first bevel gear meshes with the second bevel gear, the second bevel gear is rotatably supported, via a gear shaft, on the fixing block securely connected to the driving unit fixing plate, and the first pulley is coaxially and securely connected to the second bevel gear; the second pulley is rotatably supported on the pulley seat securely connected to the channel fixing plate; one end of the driving cable is securely connected to the first pulley, and the other end thereof passes around the second pulley and is then securely connected to the first pulley; the guiding slider is securely connected to the driving cable, the guiding slider is slidably arranged on the guiding rod, and the guiding rod is securely connected between the driving unit fixing plate and the channel fixing plate; and the guiding slider is an output end of the cable transmission mechanism.

In one embodiment, the linear motion mechanism may comprise a push-pull rod, a second guiding rod and a proximal segment driving block, wherein the second guiding rod is securely arranged between the two channel fixing plates, the proximal segment driving block is slidably connected to the second guiding rod, a front end of the push-pull rod is securely connected to the proximal segment driving block, and a rear end of the push-pull rod passes through the channel fixing plate and is securely connected to the guiding slider.

In one embodiment, the flexible surgical instrument system may further comprise a driving unit which comprises a motor part and a motion transmission part, wherein the motor part comprises a motor fixing plate and a plurality of first motors securely connected to the motor fixing plate; the motion transmission part comprises a plurality of proximal segment turning transmission chains for converting a rotational output of one of the first motors into mutually reversed rotational motions of two output shafts; and front ends of the two output shafts are directly or indirectly connected to rear ends of a pair of male couplings to transfer rotational motions of the output shafts to the male couplings.

In one embodiment, the proximal segment turning transmission chain comprises an input gear, an output gear, idle gears, and the two output shafts, the input gear is securely sheathed over one of the output shafts, the output gear is securely sheathed over the other of the output shafts, and the input gear is in transmission connection with the output gear via an even number of idle gears; and a rear end of the output shaft where the input gear is located is securely connected to an output shaft of the first motor via a coupling.

In one embodiment, a sterile barrier may be provided between the motion transmission part and the driving unit fixing plate, and the sterile barrier comprises a sterile barrier support plate, a sterile barrier cover securely connected to an outer periphery of the sterile barrier support plate, and a plurality of female couplings rotatably connected to the sterile barrier support plate, wherein a sterile membrane is securely connected to the sterile barrier cover; and a front end of each of the output shafts is securely connected to a second male coupling, and the second male coupling is connected to the male coupling via the female coupling located on the sterile barrier support plate.

In one embodiment, a cover plate may be arranged at a front end of the motion transmission part, the front end of each output shaft passes through the cover plate and is rotatably connected to the cover plate, and a first connecting pin seat is provided on the cover plate; and a second connecting pin seat configured for quick connection with the first connecting pin seat is provided on the sterile barrier support plate.

In one embodiment, a surgical end effector may be provided at a front end of the distal structural body, and a surgical end effector actuation wire connected at one end to the surgical end effector passes through the distal structural body, and is connected at the other end to a surgical end effector driving mechanism; the surgical end effector driving mechanism comprises a third male coupling rotatably arranged on the driving unit fixing plate, a front end of the third male coupling is securely connected to a threaded rod, and the threaded rod is connected, in a matching manner, to a nut; a casing is securely connected to a front side of the driving unit fixing plate, a front end of the casing is securely connected to a casing end cover, and the casing end cover is provided with an inner hole; the nut is slidably arranged in the inner hole of the casing end cover, and the inner hole limits the freedom of rotation of the nut; the nut is securely connected to a rear end of a second push-pull rod, and a front end of the second push-pull rod is securely connected to the surgical end effector actuation wire; and the motor part further comprises a second motor securely connected to the motor fixing plate, an output shaft of the second motor is securely connected to a rear end of a second output shaft via a coupling, an input gear is securely sheathed over a front end of the second output shaft, the input gear meshes with an output gear securely connected to a third output shaft, and a front end of the third output shaft is directly or indirectly connected to the third male coupling to transfer a rotational output of the second motor to the threaded rod, and to convert the rotational output into a linear motion of the nut.

In one embodiment, the flexible surgical instrument system may further comprise a flexible surgical instrument housing and a motor part housing, wherein the proximal structural body and the middle connecting body are both located in the flexible surgical instrument housing; the channel fixing plates and the driving unit fixing plate are both securely connected to the flexible surgical instrument housing; the motor part and the motion transmission part are both located in the motor part housing; a cover plate is arranged at the front end of the motion transmission part, the cover plate being securely connected to the flexible surgical instrument housing via a sterile barrier; the cover plate and the motor fixing plate are both rotatably connected to the motor part housing; and an inner ring gear is securely connected to an inner wall of the motor part housing, a third motor is securely connected to the motor fixing plate, an output shaft of the third motor is connected to a rear end of a fourth output shaft via a coupling, a front end of the fourth output shaft is securely connected to an input gear, and the input gear meshes with the inner ring gear.

In one embodiment, the flexible surgical instrument system may further comprise a flexible surgical instrument housing, a motor part housing and a linear module, wherein the proximal structural body and the middle connecting body are both located in the flexible surgical instrument housing; the channel fixing plates and the driving unit fixing plate are both securely connected to the flexible surgical instrument housing; the motor part and the motion transmission part are both located in the motor part housing; a cover plate is arranged at the front end of the motion transmission part, the cover plate being securely connected to the flexible surgical instrument housing via a sterile barrier; and the linear module comprises a support, a fourth motor securely connected to the support, and a linear feed mechanism securely connected to an output shaft of the fourth motor, an output end of the linear feed mechanism is securely connected to the motor part housing, and the fourth motor drives the motor part and the motion transmission part by means of the linear feed mechanism, to drive the flexible continuous body structure and a part, located in front of the sterile barrier, of the driving unit to perform a linear motion by means of the sterile barrier.

In one embodiment, the linear feed mechanism may comprise a lead screw rotatably connected to the support, the lead screw is sheathed with a slider which is threadedly fitted with the lead screw, a linear sliding groove is provided on the support, and the slider is slidably provided in the linear sliding groove; and the output shaft of the fourth motor is securely connected to the lead screw via a coupling.

The present invention has the following advantages due to utilizing the above technical solutions: 1. In the present invention, a flexible continuous body structure comprising a proximal structural body, a middle connecting body and a distal structural body is used as the main body, and cooperates with a driving unit, wherein the distal structural body is linked to the proximal structural body via the middle connecting body, the driving unit is linked to the proximal structural body, and when the driving unit drives the proximal structural body to turn in any direction, the distal structural body correspondingly turns in the opposite direction, so as to implement the turning motion in any direction of a flexible surgical arm formed from the distal structural body and an envelope; 2. In the present invention, a redundant arrangement of structural backbones (the number of the structural backbones being more than three) is used in the distal structural body, the middle connecting body and the proximal structural body, which can improve the stability and load capacity of the system; 3. In the present invention, a plurality of cable transmission mechanisms are provided between the driving unit fixing plate and the channel fixing plate to convert the rotational input of the male coupling into a linear motion output of the driving cable, the driving cable is securely connected to one end of the push-pull rod via the guiding slider, the other end of the push-pull rod is connected to one end of the driving backbone via the proximal segment driving block, and the other end of the driving backbone passes through the proximal structural segment and is securely connected to the proximal fixing disk; and therefore, the cooperative driving of a plurality of sets of cable transmission mechanisms can turn the proximal structural segments in any direction; 4. In the present invention, the surgical end effector actuation wire of the surgical end effector passes through the distal structural body and is connected to the surgical end effector driving mechanism; in addition, a motor for driving the surgical end effector driving mechanism is provided in the motor part; and therefore, the present invention can implement the action control of the surgical end effector; 5. In the present invention, a motor part housing is further provided, the motor fixing plate and the motor part housing are connected in a rotatable manner, an inner ring gear is securely connected to an inner wall of the motor part housing, the motor part is provided with a motor which is securely connected to the motor fixing plate, an output shaft of the motor is connected to an output shaft via a coupling, one end of the output shaft is securely connected to an input gear which meshes with the inner ring gear, and the motor can thus drive the rotation of the parts, as a whole, of the system other than the motor part housing and the inner ring gear, so that the flexible surgical arm has an overall rotational freedom; 6. In the present invention, since the flexible surgical instrument housing is connected to the motor part and the motion transmission part via a sterile barrier, thereby effectively isolating a sterilized part, such as the flexible surgical instrument, located in front of the sterile barrier from other unsterilized parts located behind the sterile barrier, and the feasibility of clinical surgery can be thus ensured; and 7. In the present invention, a linear module is further provided, which is partially connected to the motor part housing and can drive the flexible surgical instrument, the driving unit and the sterile barrier to perform a linear motion, so that the flexible surgical arm also has a linear feed freedom.

The present invention can be applied to the single-port laparoscopic surgery, and can also be applied to the natural orifice transluminal non-invasive surgery.

DETAILED DESCRIPTION OF EMBODIMENTS

The present invention is to be described in detail below in conjunction with the accompanying drawings and embodiments.

Figure 1:
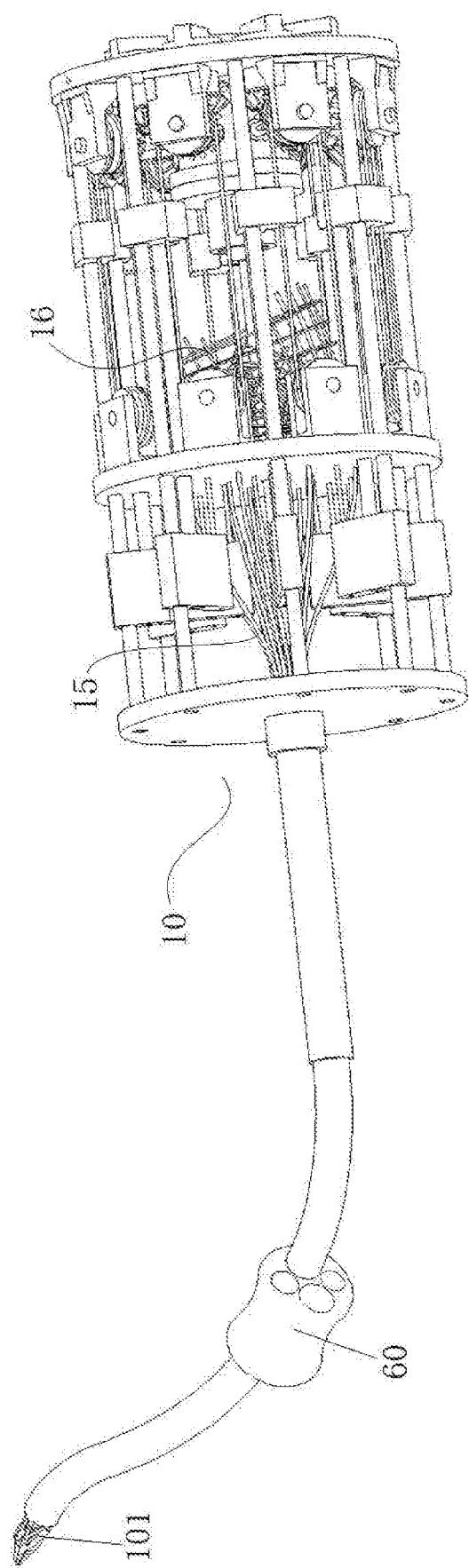
FIG. 1 is an overall structural schematic diagram according to the present invention.

As shown in FIG. 1, the present invention comprises a flexible surgical instrument 10 and a driving unit 20.

As shown in FIGS. 1 to 4, the flexible surgical instrument 10 comprises a flexible continuous body structure composed of a distal structural body 11, a proximal structural body 16 and a middle connecting body 15.

The distal structural body 11 comprises a first distal structural segment 12 and a second distal structural segment 13, wherein the first distal structural segment 12 comprises first distal spacing disks 121, a first distal fixing disk 122 and first segment structural backbones 123. The second distal structural segment 13 comprises second distal spacing disks 131, a second distal fixing disk 132 and second segment structural backbones 133. The first distal spacing disks 121 and the second distal spacing disks 131 are respectively distributed at intervals in the first distal structural segment 12 and the second distal structural segment 13, which functions to prevent the first segment structural backbones 123 and the second segment structural backbones 133 from being destabilized when being pushed.

Figure 3:
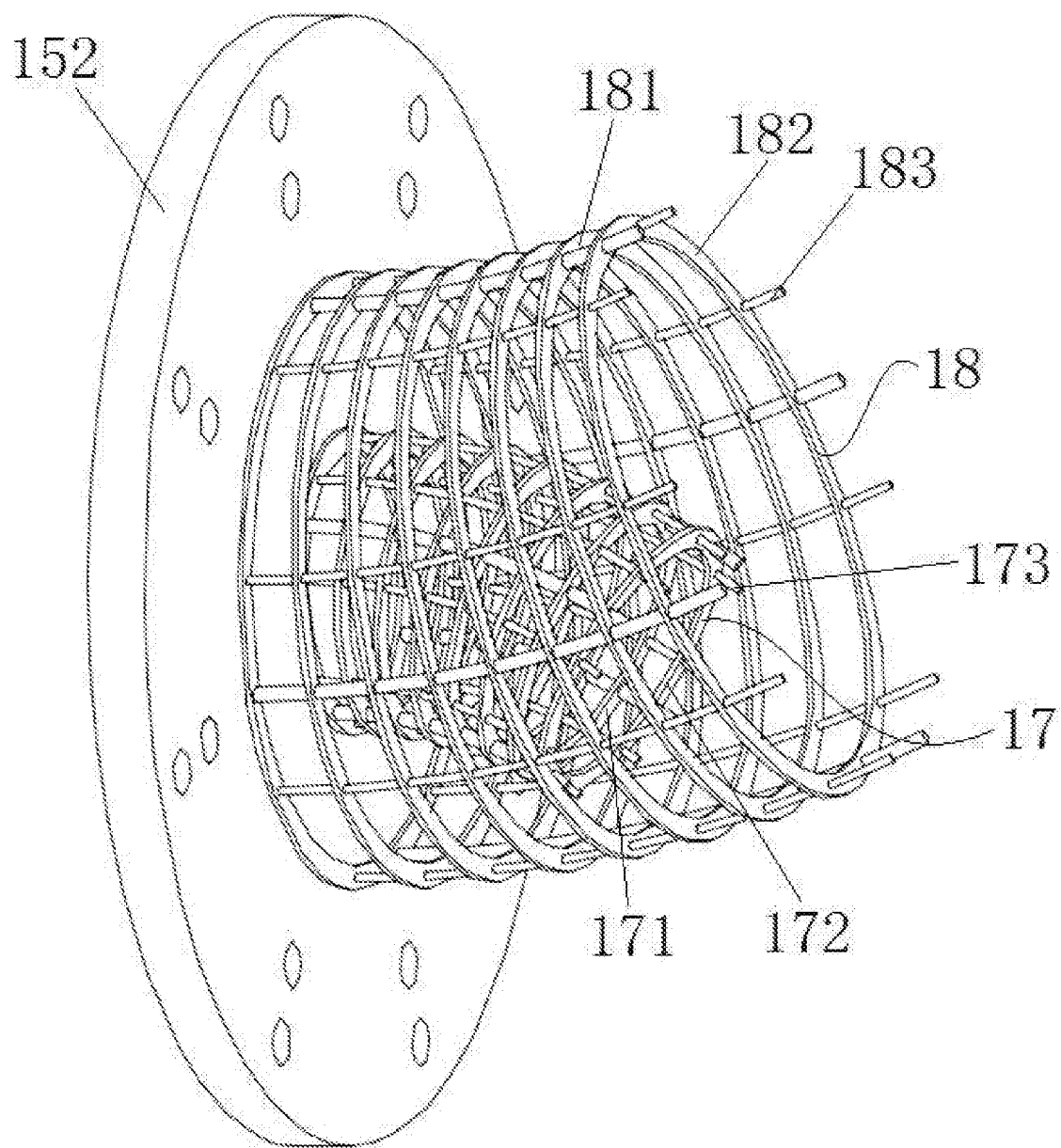
FIG. 3 is a structural schematic diagram of a proximal structural body according to the present invention.
Figure 4:
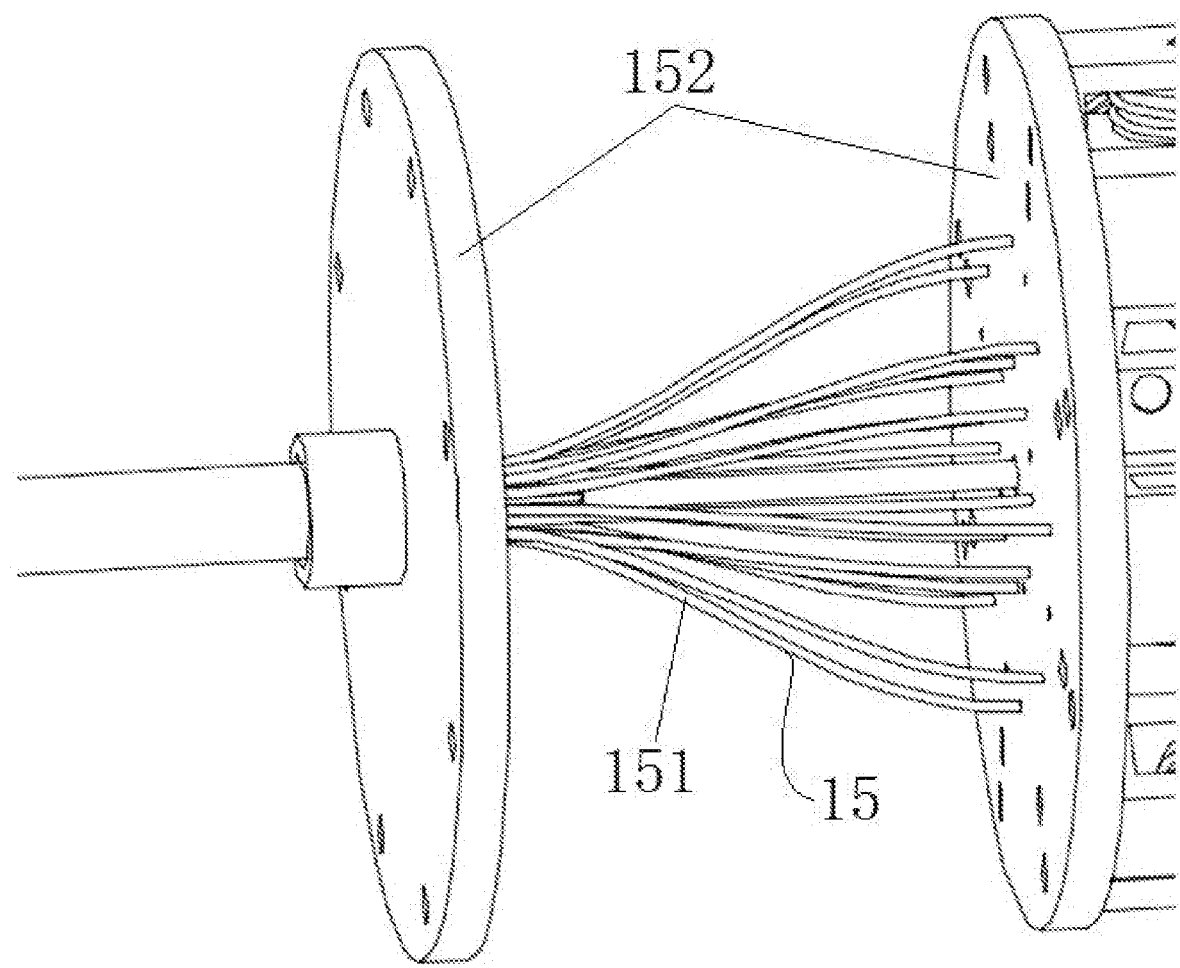
FIG. 4 is a structural schematic diagram of a middle connecting body according to the present invention.

The proximal structural body 16 comprises a first proximal structural segment 17 and a second proximal structural segment 18, as shown in FIG. 3, wherein the first proximal structural segment 17 comprises first proximal spacing disks 171, a first proximal fixing disk 172 and first segment structural backbones 173; and the second proximal structural segment 18 comprises second proximal spacing disks 181, a second proximal fixing disk 182, and second segment structural backbones 183. The first proximal spacing disks 171 and the second proximal spacing disks 181 are respectively distributed at intervals in the first proximal structural segment 17 and the second proximal structural segment 18, which functions to prevent the first segment structural backbones 173 and the second segment structural backbones 183 from being destabilized when being pushed. The first segment structural backbones 173 of the first proximal structural segment 17 are securely connected, in one-to-one correspondence, to, or are the same as the first segment structural backbones 123 of the first distal structural segment 12; and the second segment structural backbones 183 of the second proximal structural segment 18 are securely connected, in one-to-one correspondence, to, or are the same as the second segment structural backbones 133 of the second distal structural segment 13. For each of the proximal structural segments 17, 18 or of the distal structural segments 12, 13, the number of structural backbones is three or more.

The middle connecting body 15 comprises channel fixing plates 152 and structural backbone guide channels 151 securely connected between the channel fixing plates 152. One end of the first segment structural backbone 173 (123) is securely connected to the first proximal fixing disk 172, and the other end thereof passes through the first proximal spacing disks 171, the structural backbone guide channel 151 and the first distal spacing disks 121 in sequence and is then securely connected to the first distal fixing disk 122. One end of the second segment structural backbone 183 (133) is securely connected to the second proximal fixing disk 182, and the other end thereof passes through the second proximal spacing disks 181, the structural backbone guide channel 151, the first distal structural segment 12 and the second distal spacing disks 131 in sequence and is then securely connected to the second distal fixing disk 132. The structural backbone guide channel 151 functions to maintain the shape of the first segment structural backbone 173 (123) and the second segment structural backbone 183 (133) under a pushing or pulling force.

The number of the distal structural segments comprised in the distal structural body 11 and the number of the proximal structural segments comprised in the proximal structural body 16 may also be one or more than two, but the number of the proximal structural segments is always consistent with the number of the distal structural segments. In addition, when the number of the distal structural segments is two or more, the distal structural segments are connected in series, that is, the second segment structural backbone passes through the first distal fixing disk and the first distal spacing disks (and can also pass through the first segment structural backbone if the first segment structural backbone is of a tubular structure). When the number of the proximal structural segments is two or more, series connection, independent arrangement, nested arrangement, etc. may be applied between the structural segments. In this embodiment, the nested arrangement is used between the two proximal structural segments (as shown in FIG. 3).

Figure 5:
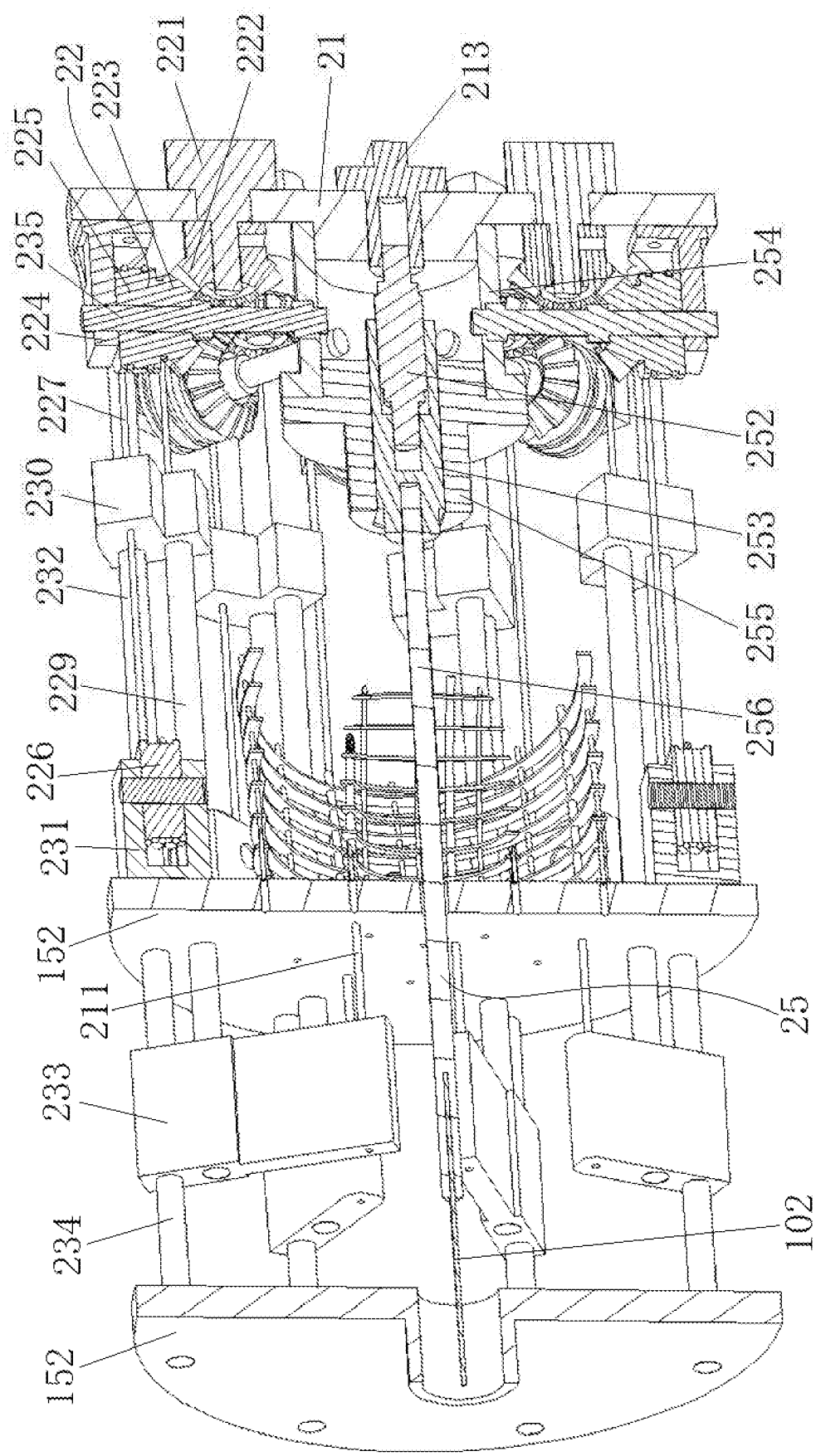
FIG. 5 is a structural schematic diagram of a longitudinal section of a flexible surgical instrument according to the present invention with the distal structural body omitted.

As shown in FIG. 5, a driving unit fixing plate 21 is arranged behind the channel fixing plate 152, and a plurality of cable transmission mechanisms 22 is arranged between the driving unit fixing plate 21 and the channel fixing plate 152, each of the cable transmission mechanisms 22 comprising a male coupling 221, two bevel gears 222, 223, a gear shaft 235, a fixing block 224, two pulleys 225, 226, a pulley seat 231, a driving cable 227, a guiding rod 232, a push-pull rod 229, and a guiding slider 230. The male coupling 221 is rotatably arranged on the driving unit fixing plate 21 and the front end thereof is coaxially and securely connected to the bevel gear 222, the bevel gear 222 meshes with the bevel gear 223, and the bevel gear 223 is rotatably supported, via the gear shaft 235, on the fixing block 224 securely connected to the driving unit fixing plate 21; the pulley 225 is coaxially and securely connected to the bevel gear 223; the pulley 226 is rotatably supported on the pulley seat 231 securely connected to the channel fixing plate 152; one end of the driving cable 227 is securely connected to the pulley 225, and the other end thereof passes around the pulley 226 and is then securely connected to the pulley 225. The guiding slider 230 is securely connected to the driving cable 227, and the guiding slider 230 is slidably disposed on the guiding rod 232. The guiding rod 232 is securely connected between the driving unit fixing plate 21 and the channel fixing plate 152. The guiding slider 230 is securely connected to the rear end of the push-pull rod 229, the front end of the push-pull rod 229 passes through the channel fixing plate 152 and is connected to one end of the driving backbone 211 via the proximal segment driving block 233, and the other end of the driving backbone 211 passes through the first proximal spacing disks 171 and is then securely connected to the first proximal fixing disk 172, or passes through the second proximal spacing disks 181 and is then securely connected to the second proximal fixing disk 182. A guiding rod 234 is securely arranged between the two channel fixing plates 152, and the proximal segment driving block 233 is slidably connected to the guiding rod 234. In a preferred embodiment, the guiding rod 234 and the guiding rod 232 are of the same guiding rod.

When the male coupling 221 is driven to rotate, the male coupling 221 transfers the rotational motion to the pulley 225 through the bevel gears 222, 223, and the pulley 225 pulls the driving cable 227, so that the guiding slider 230 performs a linear motion along the guiding rod 232, the proximal segment driving slider 233 performs a linear motion along the guiding rod 234 by means of the push-pull rod 229, and in turn the driving backbone 211 is pushed or pulled to drive the first proximal structural segment 17 or the second proximal structural segment 18 to turn. The cooperative driving of a plurality of sets of cable transmission mechanisms 22 (eight in this embodiment) can realize the cooperative pushing or pulling of a plurality of driving backbones 211 (eight in this embodiment), thereby driving the proximal structural segments 17, 18 to turn in any direction.

Figure 6:
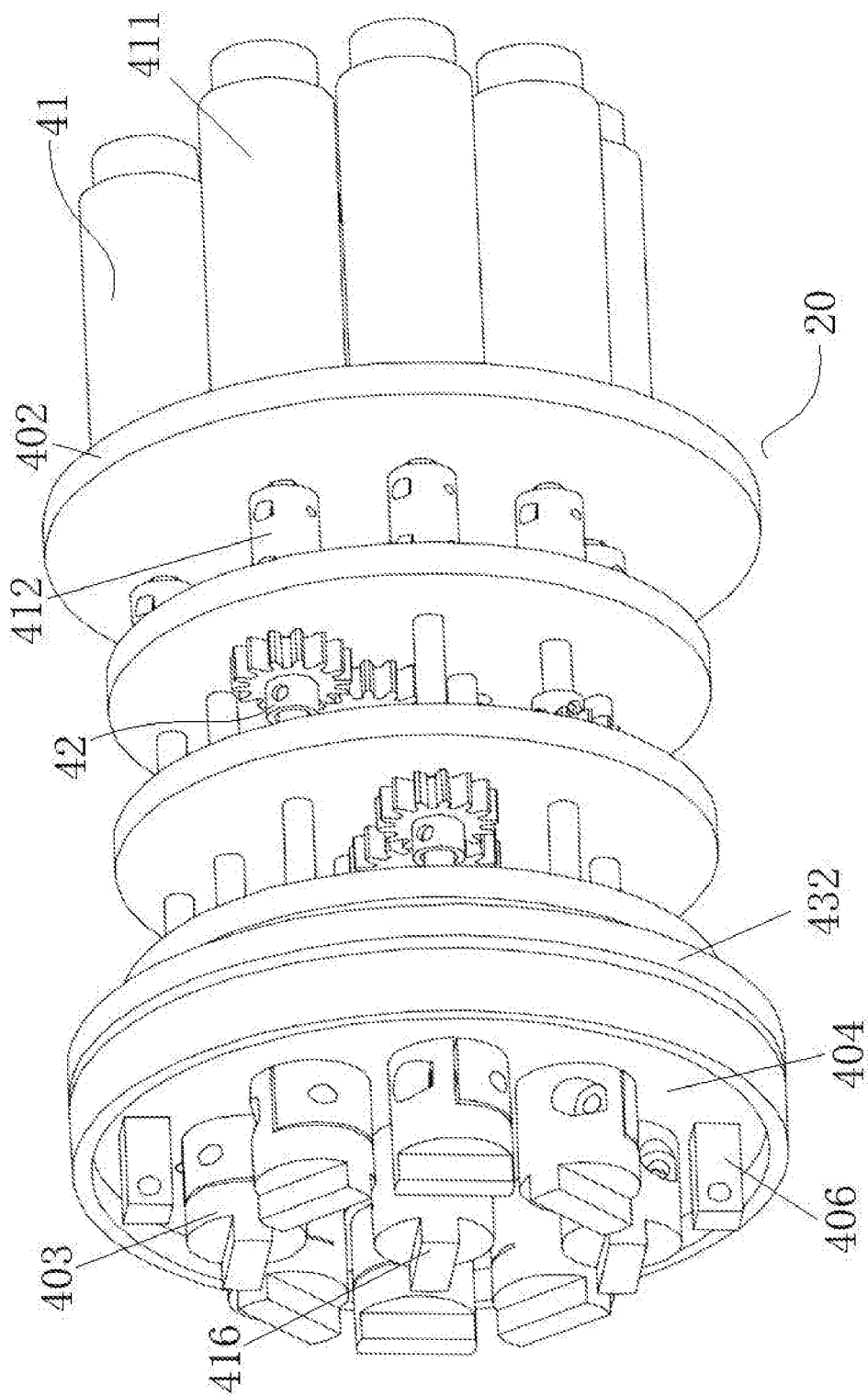
FIG. 6 is a structural schematic diagram of a driving unit according to the present invention.
Figure 7:
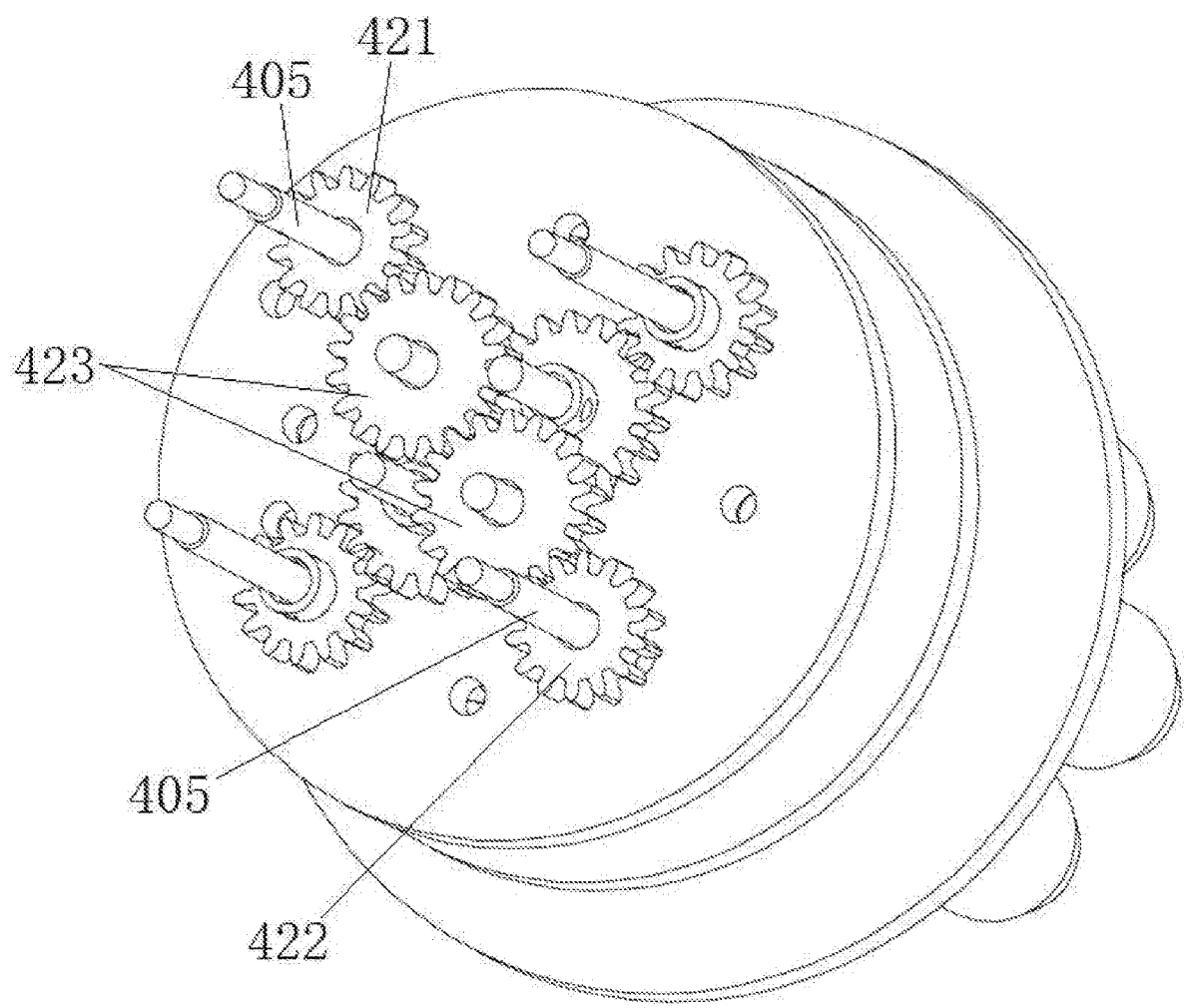
FIG. 7 is a structural schematic diagram of a proximal segment turning transmission chain according to the present invention.

As shown in FIGS. 6 and 7, the driving unit 20 comprises a motor part 41 and a motion transmission part. The motor part 41 comprises a motor fixing plate 402 and a plurality of first motors 411 securely connected to the motor fixing plate 402. The motion transmission part comprises a plurality of proximal segment turning transmission chains 42, each of the proximal segment turning transmission chains 42 is connected to an output shaft of one of the first motors 411 via a coupling 412 for decomposing the rotational output of the first motor 411 into mutually reversed rotational motions of two output shafts 405, so as to transfer the same to a pair of male couplings 221 to achieve the cooperative pushing or pulling of the proximal structural segments. The proximal segment turning transmission chains 42 each comprises an input gear 421, an output gear 422, two (even number) idle gears 423, and two output shafts 405, and the input gear 421 is securely sheathed on one of the output shafts 405, the rear end of the output shaft 405 is connected to the output shaft of the first motor 411 via the coupling 412; and the output gear 422 is securely sheathed on the other output shaft 405, and the input gear 421 is in transmission connection with the output gear 422 via the two (even number) idle gears 423. The front end of each output shaft 405 is directly or indirectly connected to one of the male couplings 221, whereby two cable transmission mechanisms 22 can be moved by the rotational output of one first motor 411, thereby driving the first proximal structural segment 17 or the second proximal structural segment 18 to turn in a certain direction.

Figure 8:
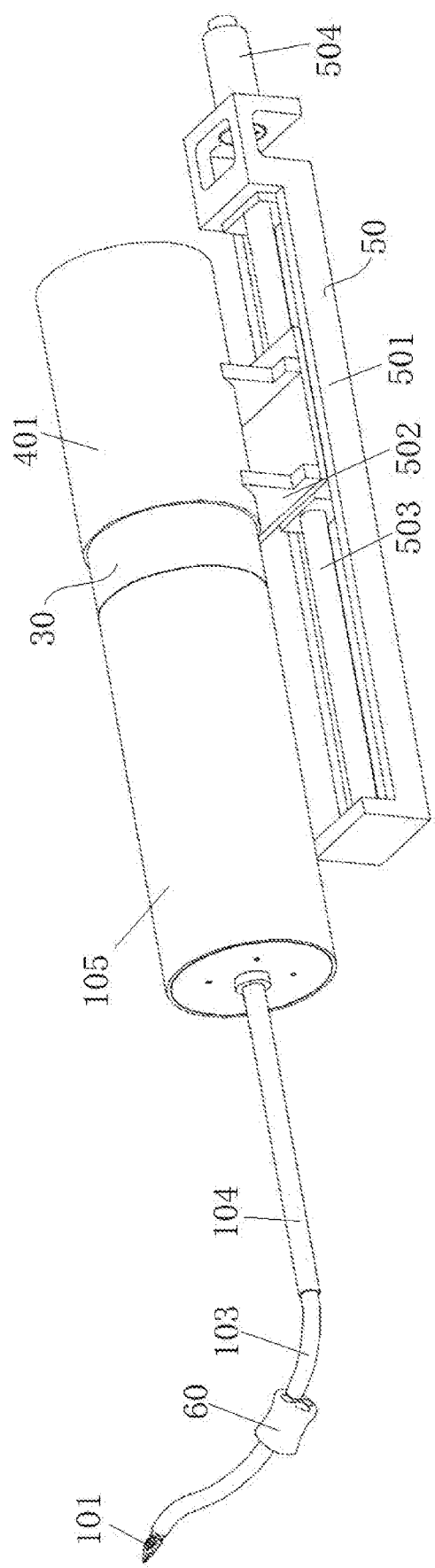
FIG. 8 is a structural schematic view according to the present invention with a flexible surgical instrument housing, a motor part housing, a sterile barrier and a linear module installed.
Figure 9:
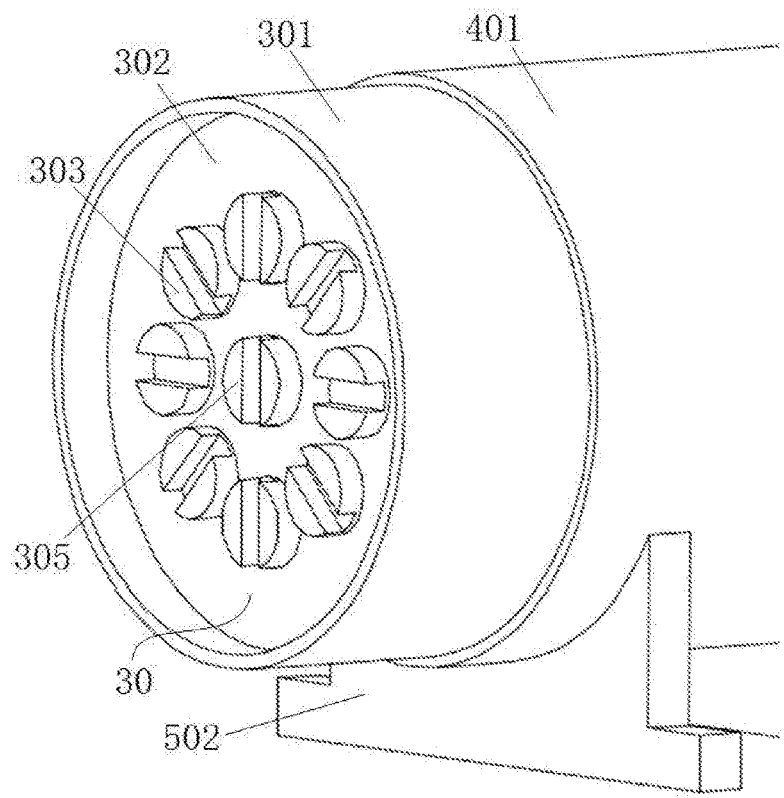
FIG. 9 is a structural schematic diagram of the sterile barrier connected to a cover plate according to the present invention.
Figure 10:
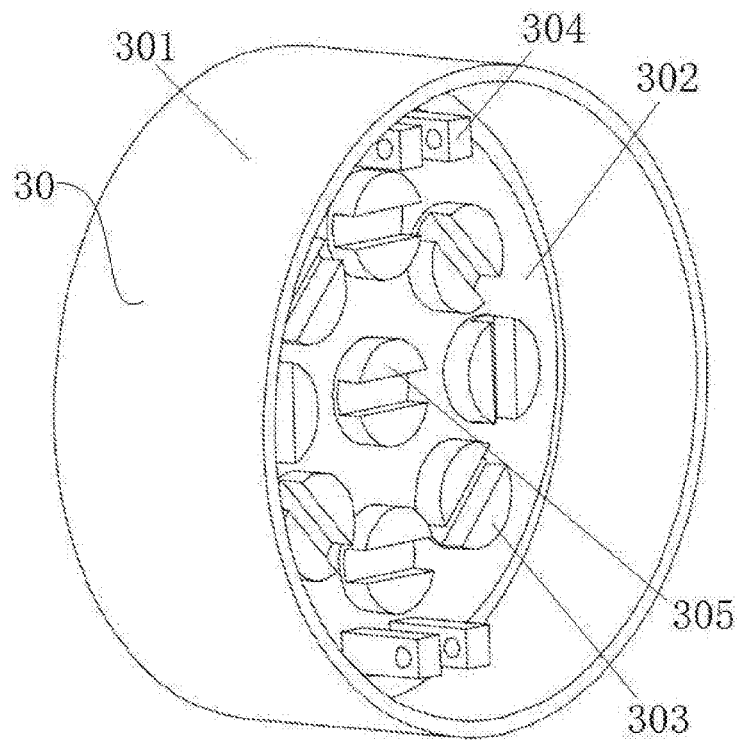
FIG. 10 is a structural schematic diagram of the sterile barrier according to the present invention, but viewed from another angle.

In the above embodiment, as shown in FIGS. 8 to 10, a sterile barrier 30 is provided between the motion transmission part and the driving unit fixing plate 21, and the sterile barrier 30 comprises a sterile barrier support plate 302, a sterile barrier cover 301 securely connected to an outer periphery of the sterile barrier support plate 302, and a plurality of female couplings 303 rotatably connected to the sterile barrier support plate 302, the front ends of the female couplings 303 being configured to be connected to the male couplings 221. A male coupling 403 (as shown in FIG. 6) configured to be connected to the rear end of the female coupling 303 is securely connected to the front end of each output shaft 405. The rotational motion of the output shaft 405 can thus be transferred to the bevel gear 222 via the male coupling 403, the female coupling 303, and the male coupling 221. A sterile membrane (not shown) is securely connected to the sterile barrier cover 301, which can isolate a sterilized part, such as the flexible surgical instrument 10 that is located in front of the sterile barrier 30, from unsterilized parts, such as the motion transmission part and the motor part 41 behind the sterile barrier 30, to ensure the feasibility of clinical surgery.

In the above embodiment, as shown in FIGS. 6 and 10, a cover plate 404 is arranged at the front end of the motion transmission part, the front end of each output shaft 405 passes through the cover plate 404 and is rotatably connected to the cover plate 404, and two sets of connecting pin seats 406 are provided on the cover plate 404; and correspondingly, two sets of connecting pin seats 304 configured for quick connection to the connecting pin seats 406 are also provided on the sterile barrier support plate 302. In this way, the sterile barrier 30 is fixedly connected to the motion transmission part and can transfer the overall motion.

Figure 2:
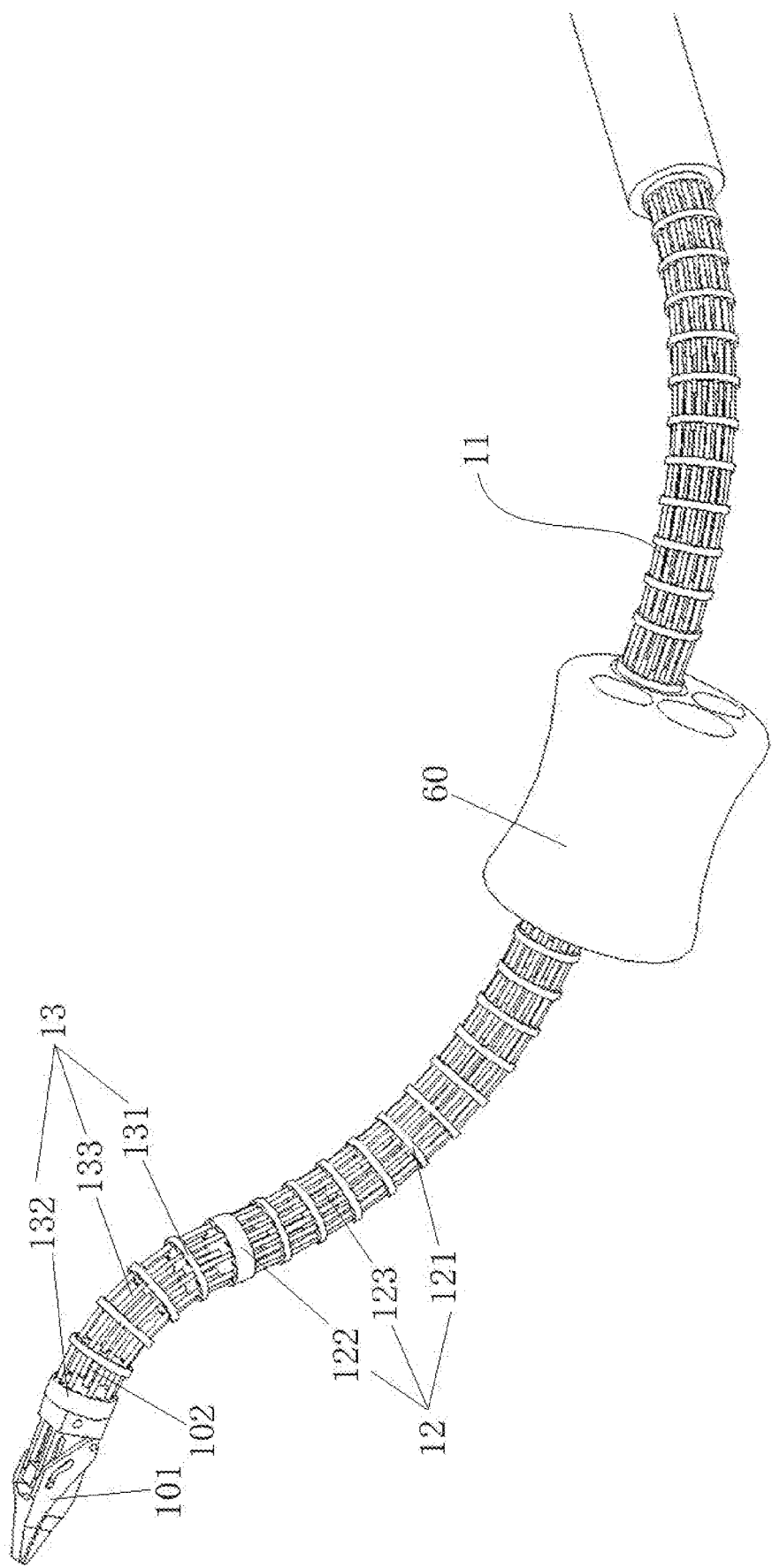
FIG. 2 is a structural schematic diagram of a distal structural body according to the present invention.
Figure 11:
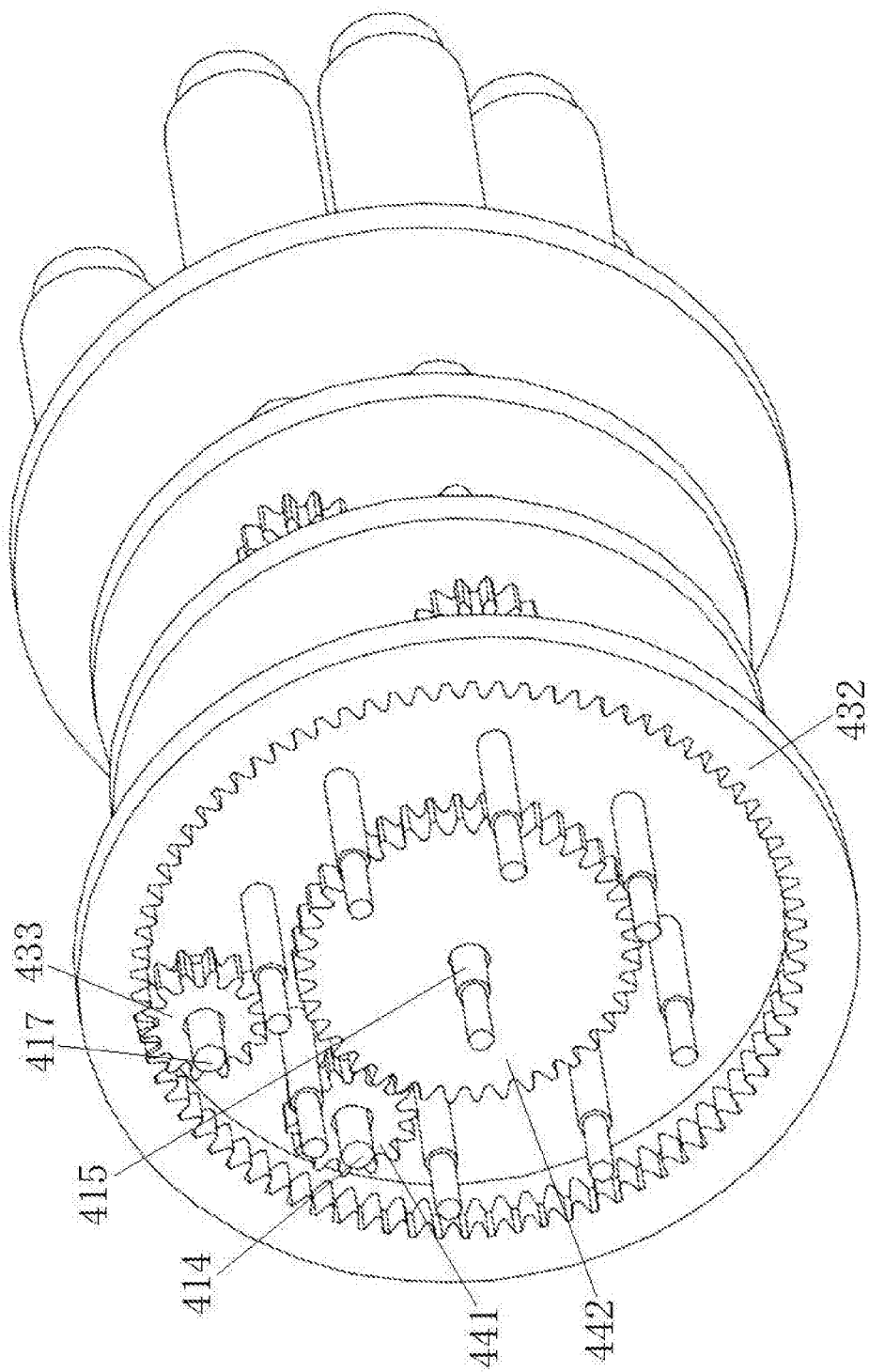
FIG. 11 is a structural schematic diagram of an overall rotation driving mechanism according to the present invention.

In the above embodiment, as shown in FIGS. 2, 5 and 11, a surgical end effector 101 is provided at the front end of the distal structural body 11, and a surgical end effector actuation wire 102 connected at one end to the surgical end effector 101 passes through the distal structural body 11, and is connected at the other end to a surgical end effector driving mechanism 25. The surgical end effector driving mechanism 25 comprises a male coupling 213 rotatably arranged on the driving unit fixing plate 21, and the front end of the male coupling 213 is securely connected to a threaded rod 252, and the threaded rod 252 is connected, in a matching manner, to a nut 253. Further, a casing 254 is securely connected to the front side of the driving unit fixing plate 21, the front end of the casing 254 is securely connected to a casing end cover 255, and the casing end cover 255 is provided with an inner hole. The nut 253 is slidably arranged in the inner hole of the casing end cover 255, and the inner hole is preferably a square hole so that the nut 253 can only freely slide but cannot rotate in the inner hole. The nut 253 is securely connected to the rear end of a push-pull rod 256, and the front end of the push-pull rod 256 is securely connected to the rear end of the surgical end effector actuation wire 102. A second motor is securely connected to the motor fixing plate 402, an output shaft of the second motor is securely connected to the rear end of an output shaft 414 via the coupling 412, an input gear 441 is securely sheathed over the front end of the output shaft 414, the input gear 441 meshes with an output gear 442, the output gear 442 is securely connected to an output shaft 415, and the front end of the output shaft 415 is directly or indirectly connected to the male coupling 213 to transfer the rotational output of the second motor to the threaded rod 252, thereby converting the same into the linear motion of the nut 253, so that the surgical end effector actuation wire 102 is pushed or pulled by the push-pull rod 256 to control the surgical end effector 101 (e.g., surgical forceps) to perform actions. The surgical end effector actuation wire 102 may also transfer various forms of energy, such as electrical energy and high-frequency vibrations, to achieve specific surgical functions (e.g., electrocoagulation, and electric resection) of the surgical end effector 101. Further, the front end of the output shaft 415 is securely connected to a male coupling 416 (as shown in FIG. 6), and the male coupling 416 is connected to the male coupling 213 via a female coupling 305 located on the sterile barrier 30 (as shown in FIGS. 9 and 10).

Figure 12:
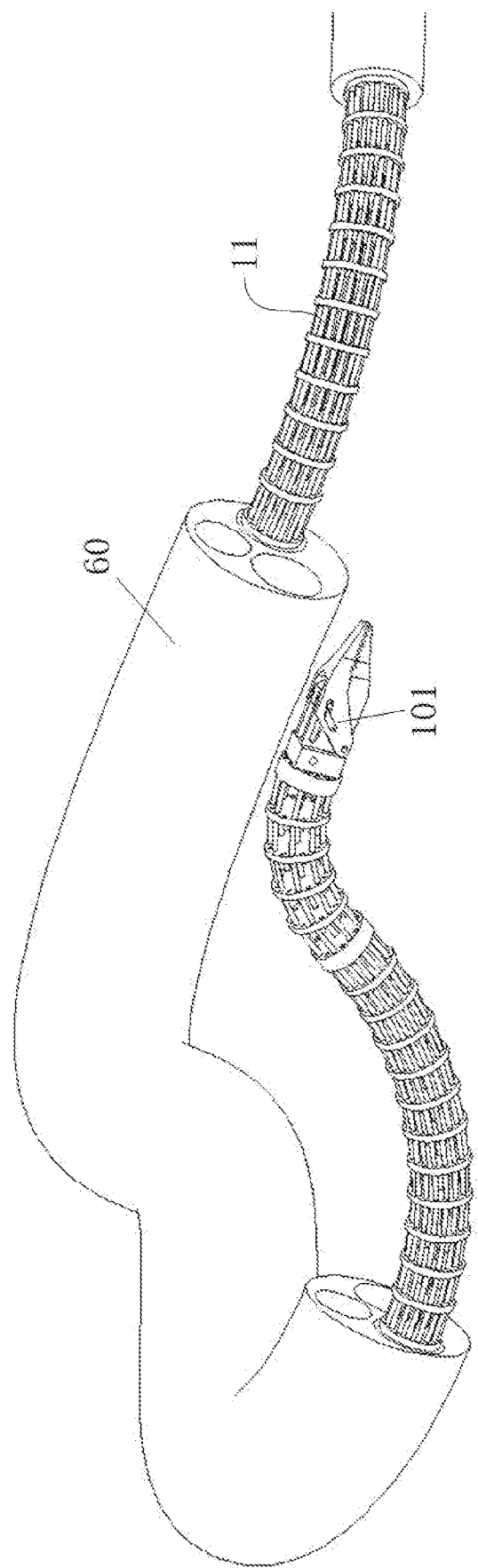
FIG. 12 is a structural schematic diagram of the distal structural body using a flexible sheath according to the present invention.

In the above embodiment, as shown in FIGS. 8 and 12, the present invention further comprises a flexible surgical instrument housing 105 and a motor part housing 401. The proximal structural body 16 and the middle connecting body 15 are both located in the flexible surgical instrument housing 105; and the channel fixing plate 152 and the driving unit fixing plate 21 are both securely connected to the flexible surgical instrument housing 105. The motor part 41 and the motion transmission part are both located in the motor part housing 401; and the cover plate 404 at the front end of the motion transmission part is securely connected to the flexible surgical instrument housing 105 via the sterile barrier 30, so that the flexible surgical instrument 10 can rotate integrally with the motion transmission part and the motor part 41. The cover plate 404 and the motor fixing plate 402 are both rotatably connected to the motor part housing 401. An inner ring gear 432 is securely connected to an inner wall of the motor part housing 401, and a third motor is securely connected to the motor fixing plate 402. An output shaft of the third motor is connected to the rear end of an output shaft 417 via the coupling 412, the front end of the output shaft 417 is securely connected to an input gear 433, and the input gear 433 meshes with the inner ring gear 432. When the output shaft of the third motor rotates, the input gear 433 is driven to rotate, and the input gear 433 travels in a circumferential direction of the inner ring gear 432, thereby driving the rotation of the parts, as a whole, of the present invention other than the motor part housing 401 and the inner ring gear 432, and achieving control over the roll angle of the surgical end effector 101.

In the above embodiment, as shown in FIG. 8, the present invention further comprises a linear module 50 (the linear module 50 also being isolated from the sterilized parts by the sterile membrane), which comprises a support 501 with a sliding groove, wherein a lead screw 503 is provided on the support 501, the lead screw 503 is sheathed with a slider 502 which is threadedly fitted with the lead screw 503 and slidably provided in the sliding groove, one end of the support 501 is provided with a motor 504, and an output shaft of the motor 504 is securely connected to the lead screw 503 via a coupling. The motor part housing 401 is fixedly connected to the slider 502. When the output shaft of the motor 504 rotates, the slider 502 linearly moves the driving unit 20, the sterile barrier 30 and the flexible surgical instrument 10 along the sliding groove, thereby achieving the freedom of feeding of the distal structural body 11.

In the above embodiment, as shown in FIG. 8, an envelope 103 is provided over the outside of the distal structural body 11 and functions to improve the smoothness of the distal structural body 11 entering a natural orifice or a surgical incision in the human body. A rigid outer sleeve 104 and a sheath 60 may also be provided over the outside of the envelope 103. In an application, the sheath 60 is fixed at a single incision in the abdominal cavity, and the distal structural body 11, together with the envelope 103 and the surgical end effector 101, can freely pass through a through-hole in the sheath 60 for the passage of the surgical instrument and have access to the surgical site to perform the single-port laparoscopic surgery. As shown in FIG. 12, the sheath 60 may also be a flexible sheath that can more easily extend into various natural orifices of the human body and adaptively change shape as the shape of the orifices, one end of the flexible sheath is fixed at the entrance of the orifice, and the distal structural body 11, together with the envelope 103 and the surgical end effector 101, can freely pass through a through-hole in the flexible sheath for the passage of the surgical instrument and have access to the surgical site to perform non-invasive surgery through the natural orifice.

The present invention has been illustrated only by the above embodiments, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument system, comprising:
   a distal structural body comprising at least one distal structural segment, the at least one distal structural segment comprising a distal fixing disk and structural backbones;
   a proximal structural body comprising at least one proximal structural segment, the at least one proximal structural segment comprising a proximal fixing disk, structural backbones, and driving backbones, the structural backbones of the at least one distal structural segment being securely connected in one-to-one correspondence to or the same as corresponding structural backbones of the at least one proximal structural segment;
   a plurality of cable transmission mechanisms each comprising a gear set and a pulley-cable part, the gear set being operable to transfer a rotational motion to the pulley-cable part, and the pulley-cable part being operable to drive one of guiding sliders in a linear motion to push or pull one of the driving backbones to turn the at least one proximal structural segment; and
   a driving unit comprising a motion transmission part comprising a plurality of proximal segment turning transmission chains to convert a rotational output into mutually reversed rotational motions, and transfer one of the mutually reversed rotational motions to one of the gear sets;
   a first end of the one of the driving backbones is fixed onto the proximal fixing disk, and a second end of the one of the driving backbones is connected to the one of guiding sliders.

2. The flexible surgical instrument system of claim 1, wherein
   proximal ends of the structural backbones of the at least one proximal structural segment are securely connected to the proximal fixing disk, and distal ends of the structural backbones of the at least one distal structural segment are securely connected to the distal fixing disk.

3. The flexible surgical instrument system of claim 1, wherein
   the at least one proximal structural segment further comprises proximal spacing disks, the structural backbones of the at least one proximal structural segment passing through the proximal spacing disks; and
   the at least one distal structural segment further comprises distal spacing disks, the structural backbones of the at least one distal structural segment passing through the distal spacing disks.

4. The flexible surgical instrument system of claim 1, further comprising linear motion mechanisms each comprising:
   a proximal segment driving block connected with a distal end of a corresponding driving backbone of the driving backbones; and
   a first push-pull rod comprising a first end securely connected to the proximal segment driving block and a second end securely connected to a guiding slider of the guiding sliders.

5. The flexible surgical instrument system of claim 1, wherein one of the pulley-cable parts comprises:
   a first pulley connected with the one of the gear sets and operable to receive rotational motion transferred from the one of the gear sets;
   a second pulley; and
   a driving cable passing around the second pulley and comprising a first end securely connected to one side of the first pulley and second end securely connected to another side of the first pulley; the one of the guiding sliders is securely connected to the driving cable.

6. The flexible surgical instrument system of claim 5, wherein the one of the gear sets comprises:
   a first bevel gear; and
   a second bevel gear meshing with the first bevel gear; and
   the second bevel gear is coaxially and securely connected to the first pulley, and the first bevel gear is operable to transfer the rotational motion to the second bevel gear.

7. The flexible surgical instrument system of claim 6, wherein one of the plurality of cable transmission mechanisms comprises:
   a coupling coaxially and securely connected to the first bevel gear.

8. The flexible surgical instrument system of claim 1, further comprising:
   a middle connecting body comprising channel fixing plates and structural backbone guide channels arranged between the channel fixing plates, and
   the structural backbones of the at least one distal structural segment pass through the structural backbone guide channels and the distal ends of the structural backbones of the at least one distal structural segment are securely connected to the distal fixing disk.

9. The flexible surgical instrument system of claim 1, further comprising:
   a surgical end effector provided at a distal end of the distal structural body;
   a surgical end effector actuation wire passing through the distal structural body, the surgical end effector actuation wire comprising a proximal end securely connected to a surgical end effector driving mechanism and a distal end securely connected to the surgical end effector.

10. The flexible surgical instrument system of claim 9, wherein the surgical end effector driving mechanism comprises:
    a threaded rod;
    a nut in threaded connection with the threaded rod; and
    a second push-pull rod comprising a proximal end securely connected to the nut and a distal end securely connected to the surgical end effector actuation wire.

11. The flexible surgical instrument system of claim 1, wherein the driving unit comprises:
a motor part comprising a motor fixing plate and a plurality of first motors are securely connected to the motor fixing plate, one of the plurality of first motors operable to output the rotational output; one of two output shafts being operable to transfer the one of the mutually reversed rotational motions to the one of the gear sets.

12. The flexible surgical instrument system of claim 11, wherein one of the plurality of proximal segment turning transmission chains comprises:
an input gear securely sheathed over the one of the two output shafts which is securely connected to the one of the plurality of first motors;
an output gear securely sheathed over another one of the two output shafts; and
idle gears, the input gear being in transmission connection with the output gear via the idle gears.

13. The flexible surgical instrument system of claim 11, further comprising:
a sterile barrier fixedly connected to the motion transmission part and provided between the plurality of cable transmission mechanisms and the motion transmission part.

14. The flexible surgical instrument system of claim 13, wherein the sterile barrier comprises:
a sterile barrier support plate;
a sterile barrier cover securely connected to an outer periphery of the sterile barrier support plate; and
a plurality of couplings rotatably connected to the sterile barrier support plate.

15. The flexible surgical instrument system of claim 14, wherein the motion transmission part comprises:
a cover plate arranged at a distal end of the motion transmission part; and a first connecting pin seat provided on the cover plate, and
the sterile barrier support plate comprises a second connecting pin seat connected with the first connecting pin seat.

16. The flexible surgical instrument system of claim 11, further comprising:
a flexible surgical instrument housing, the proximal structural body being located in the flexible surgical instrument housing;
a motor part housing;
a cover plate arranged at a distal end of the motion transmission part, the cover plate and the motor fixing plate being rotatably connected to the motor part housing and the cover plate being securely connected to the flexible surgical instrument housing via a sterile barrier;
an inner ring gear securely connected to an inner wall of the motor part housing and meshing with an input gear, and
a third motor securely connected to the motor fixing plate, an output shaft of the third motor being connected to a proximal end of a fourth output shaft, a distal end of the fourth output shaft being securely connected with the input gear.

17. The flexible surgical instrument system of claim 1, further comprising a linear module to drive the flexible surgical instrument and the driving unit to perform a linear motion.

18. The flexible surgical instrument system of claim 17, wherein the linear module comprises a fourth motor and a linear feed mechanism, the linear feed mechanism comprising a lead screw sheathed with a slider which is threaded fit with the lead screw and an output shaft of the fourth motor being connected to the lead screw.

* * * * *